United States Patent [19]

Jones et al.

[11] Patent Number: 4,523,050

[45] Date of Patent: Jun. 11, 1985

[54] METHANE CONVERSION PROCESS

[75] Inventors: C. Andrew Jones, Newtown Square; John A. Sofranko, Malvern, both of Pa.

[73] Assignee: Atlantic Richfield Company, Los Angeles, Calif.

[21] Appl. No.: 600,670

[22] Filed: Apr. 16, 1984

[51] Int. Cl.$^3$ ................................................ C07C 2/00
[52] U.S. Cl. ................................. 585/500; 585/415; 585/417; 585/418; 585/541; 585/654; 585/658; 585/661; 585/943; 585/700
[58] Field of Search ............... 585/500, 417, 418, 415, 585/654, 656, 658, 661, 541, 943, 700

[56] References Cited

U.S. PATENT DOCUMENTS

| | | | |
|---|---|---|---|
| 4,205,194 | 5/1980 | Mitchell et al. | 585/500 |
| 4,239,658 | 12/1980 | Mitchell et al. | 585/500 |
| 4,443,645 | 4/1984 | Jones et al. | 585/500 |
| 4,443,648 | 4/1984 | Jones et al. | 585/500 |

FOREIGN PATENT DOCUMENTS 368257  8/1931  United Kingdom ................ 585/943

OTHER PUBLICATIONS

Keller, G. E., "Synthesis of Ethylene via Oxidative Coupling of Methane", J. of Catalysis, 73, 9–19, (1982).

*Primary Examiner*—Delbert E. Gantz
*Assistant Examiner*—Cynthia A. Prezlock
*Attorney, Agent, or Firm*—Craig E. Larson

[57] ABSTRACT

An improved method for converting methane to higher hydrocarbon products by contacting a hydrocarbon gas comprising methane, an oxygen-containing gas and a reducible metal oxide under synthesis conditions, the improvement which comprises contacting methane and oxygen with a contact solid which comprises at least one manganese silicate.

15 Claims, No Drawings

METHANE CONVERSION PROCESS

BACKGROUND OF THE INVENTION

This invention relates to the synthesis of hydrocarbons from a methane source. A particular application of this invention is a method for converting natural gas to more readily transportable material.

A major source of methane is natural gas. Other sources of methane have been considered for fuel supply, e.g., the methane present in coal deposits or formed during mining operations. Relatively small amounts of methane are also produced in various petroleum processes.

The composition of natural gas at the wellhead varies but the major hydrocarbon present is methane. For example, the methane content of natural gas may vary within the range from about 40 to about 95 volume percent. Other constituents of natural gas include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_{3}+$ hydrocarbons carbons although some ethane may be included. Gas conditioning is required to alter the composition of wellhead gas, processing facilities usually being located in or near the production fields. Conventional processing of wellhead natural gas yields processed natural gas containing at least a major amount of methane.

Large scale use of natural gas often requires a sophisticated and extensive pipeline system. Liquefaction has also been employed as a transportation means, but processes for liquefying, transporting, and revaporizing natural gas are complex, energy-intensive and require extensive safety precautions. Transport of natural gas has been a continuing problem in the exploitation of natural gas resources. It would be extremely valuable to be able to convert methane (e.g., natural gas) to more readily handleable or transportable products. Moreover, direct conversion of olefins such as ethylene or propylene would be extremely valuable to the chemical industry.

Recently, it has been discovered that methane may be converted to higher hydrocarbons (e.g., ethane, ethylene and higher homologs) by contacting methane with a reducible metal oxide as a selective oxygen source. As the methane is converted to hydrocarbon products and coproduct water, the active oxygen of the metal oxide is depleted, resulting in a reduced metal oxide. The reduced metal oxide is relatively inactive for the oxidative conversion of methane but active oxygen may be replaced by regenerating of a reducible metal oxide. Such regeneration is accomplished by reoxidation of the reduced metal oxide.

Reducible oxides of several metals have been identified which are capable of converting methane to higher hydrocarbons. Oxides of manganese, tin, indium, germanium, lead, antimony and bismuth are particularly useful. See commonly-assigned U.S. patent application Ser. Nos. 522,925 (now U.S. Pat. No. 4,443,649); 522,944 (now U.S. Pat. No. 4,444,984); 522,942 (now U.S. Pat. No. 4,443,648); 522,905 (now U.S. Pat. No. 4,443,645); 522,877 (now U.S. Pat. No. 4,443,647); 522,876 (now U.S. Pat. No. 4,443,644); and 522,906 (now U.S. Pat. No. 4,443,646), all filed Aug. 12, 1983, the entire contents of each being incorporated herein by reference.

Commonly-assigned U.S. patent application Ser. No. 522,935, filed Aug. 12, 1983, discloses and claims a process which comprises contacting methane with an oxidative synthesizing agent under elevated pressure (e.g., 2-100 atmospheres) to produce greater amounts of $C_{3}+$ hydrocarbon products.

Commonly-assigned U.S. patent application Ser. No. 522,938, filed Aug. 12, 1983, discloses and claims a process for the conversion of methane to higher hydrocarbons which comprises contacting methane with particles comprising an oxidative synthesizing agent which particles continuously recirculate between two physically separate zones—a methane contact zone and an oxygen contact zone.

In a typical application of the foregoing processes for the oxidative conversion of methane, methane feed is contacted with a reducible metal oxide and regeneration is accomplished separately by contacting the reduced metal oxide with an oxygen-containing gas (e.g., air). Thus, a cyclic redox process results in which methane reaction and reoxidation of the metal oxide "reagent" are performed separately and repeatedly for a continuous process.

Such a procedure presents several disadvantages for large scale continuous operation. One disadvantage is the large quantity of solid cycling between methane reaction and reoxidation in such a way that the methane and oxygen are not mixed. Another disadvantage is the necessity of developing a composition that is resistant to mechanical attrition and repeated exposure to reductive and oxidative environments.

Hinsen and Baerns recently reported studies of a continuous mode for the oxidative coupling of methane wherein regenerating air is cofed with the methane feed. Hinsen, W. and Bearns, M., "Oxidative Kopplung von Methan zu C$_2$-Kohlenwasserstoffen in Gegenwart unterschiedlicher Katalysatoren", Chemiker-Zeitung, Vol. 107, No. 718, pp. 223–226 (1983). Using a catalyst based on lead oxide and gamma-alumina in a fixed bed reactor operated at 1 atmosphere total pressure and 600°–750° C., they report results of approximately 53% selectivity to ethane and ethylene at 8% methane conversion for a feed consisting of about 50% methane, 25% air and 25% nitrogen. Other metal oxides studied by Hinsen and Baerns included oxides of Bi, Sb, Sn and Mn.

SUMMARY OF THE INVENTION

It has now been found that the conversion of methane to higher hydrocarbons in the presence of oxygen is improved by contacting a first, hydrocarbon gas comprising methane and a second, oxygen-containing gas with a contact solid which comprises at least one compound comprising Mn, Si and O, preferably at least one manganese silicate. Preferred manganese silicates are described by the formula $Mn_xSiO_y$ wherein x is an integer selected within the range of 1 to 7 and y has a value which is determined by the valence and proportions of the other elements present in the compound.

The improved process of the present invention produces higher methane conversion at similar hydrocarbon selectivity or increased hydrocarbon selectivity at similar methane conversion, as compared to prior methods such as that taught by Hinsen and Baerns, supra.

DETAILED DESCRIPTION OF THE INVENTION

In addition to methane the hydrocarbon feedstock employed in the method of this invention may contain other hydrocarbon or non-hydrocarbon components. The methane content of the feedstock, however, will typically be within the range of about 40 to 100 vol. %, preferably within the range of about 80 to 100 vol. %, more preferably within the range of about 90 to 100 vol. %.

The oxygen-containing gas generally comprises molecular oxygen: other gases such as nitrogen and carbon oxides may be present. A preferred oxygen-containing gas is air.

The ratio of hydrocarbon feedstock to oxygen-containing gas is not narrowly critical to the present invention. Generally, it is desirable to control the hydrocarbon/oxygen molar ratio to avoid the formation of gaseous mixtures within the flammable region. It is preferred to maintain the volume ratio of hydrocarbon/oxygen within the range of about 0.1–100:1, more preferably within the range of about 1–50:1. Methane/air feed mixtures containing about 50 to 90 volume % methane have been found to comprise a desirable feedstream. Further dilution of the feedstream with gases such as nitrogen is not necessary.

Manganese silicates suitable for use in the process of the present invention may be provided from a variety of sources. For example, the silicates are found in naturally-occurring minerals such as rhodonite ($MnSiO_3$), pyroxmangite ($MnSiO_3$), braunite ($Mn_7SiO_{12}$) or tephroite ($Mn_2SiO_4$). The silicates may also be synthesized by methods known in the art.

According to one method of synthesis, salts of manganese are mixed with silica in amounts corresponding to the desired stoichiometry, followed by heating to about 1000°–1200° C. in air. The manganese salts should be ones that thermally decompose to yield manganese oxides. Suitable salts include the acetonates, carbonates and nitrates.

In one preferred embodiment, the manganese silicates are synthesized by mixing a methanolic manganese acetate solution with tetraethoxy silane in amounts selected to provide the desired manganese to silica stoichiometry. A gel is precipitated from the resulting solution by addition of ammonium hydroxide. The gel is dried (e.g., at 100°–120° C.) and then heated (e.g., to 1000°–1200° C.) to form the manganese silicate. Particles comprising manganese silicate can be prepared from this material by standard methods.

If desired, manganese silicates may be associated support materials such as silica, alumina, titania, zirconia and the like and combinations thereof. Supported manganese silicates may be prepared by methods such as adsorption, impregnation, coprecipitation and dry mixing.

Regardless of the particular form in which manganese silicates is provided, it is desirable to calcine the contact solid at elevated temperatures in an oxygen-containing gas (e.g., air) prior to use in the process of this invention.

Preferably, methane and oxygen are contacted with solids comprising manganese silicate in the substantial absence of catalytically effective nickel, noble metals and compounds thereof. (i.e., nickel, rhodium, palladium, silver, osmium, iridium, platinum and gold) to minimize the deleterious catalytic effects thereof. These metals, when contacted with methane at the temperatures employed in the first step of the present invention, tend to promote coke formation, and the metal oxides tend to promote the formation of combustion products rather than the desired hydrocarbons. The term "catalytically effective" is used herein to identify that quantity of one or more of nickel and of the noble metals and compounds thereof which substantially changes the distribution of products obtained in the method of this invention relative to such contacting in the absence of such metals and compounds thereof.

Operating temperatures for the method of this invention are generally within the range of about 300° to 1200° C., more preferably within the range of about 500° to 1000° C.

Operating pressures are not critical to the presently claimed invention. However, both general system pressure and partial pressures of methane and oxygen have been found to effect overall results. Preferred operating pressures are within the range of about 0.1 to 30 atmospheres.

The space velocity of the gaseous reaction streams are similarly not critical to the presently claimed invention, but have been found to effect overall results. Preferred total gas hourly space velocities are within the range of about 10 to 100,000 hr.$^{-1}$, more preferably within the range of about 600 to 40,000 hr.$^{-1}$.

The solid which is contacted with methane and oxygen according to the present process has heretofore been generally referred to as an oxidative synthesizing agent. Oxidative synthesizing agents comprise at least one oxide of at least one metal, which oxides when contacted with methane at temperatures selected within the range of about 500° to 1000° C. produce higher hydrocarbon products, coproduct water and a reduced metal oxide. The composition thus contains at least one reducible oxide of at least one metal. The term "reducible" identifies those oxides of metals which are reduced by the methane contact. The term "oxide(s) of metal(s)" includes: (1) one or more metal oxides (e.g., compounds described by the general formula $M_xO_y$ wherein M is a metal and the subscripts x and y designate the relative atomic proportions of metal and oxide in the composition) and/or (2) one or more oxygen-containing metal compounds, provided that such oxides and compounds have the capability of performing to produce higher hydrocarbon products as described.

Contacting methane and a reducible metal oxide to form higher hydrocarbons from methane also produces coproduct water and reduces the metal oxide. The exact nature of the reduced metal oxides are unknown, and so are referred to as "reduced metal oxides". Regeneration of reducible metal oxides in the method of the present invention occurs "in situ"—by contact of the reduced metal oxide with the oxygen cofed with methane to the contact zone.

The contact solids may be maintained in the contact zone as fixed, moving, or fluidized beds of solids. A fixed bed of solids is currently preferred for the method of this invention.

The effluent from the contact zone contains higher hydrocarbon products (e.g., ethylene, ethane and other light hydrocarbons), carbon oxides, water, unreacted hydrocarbon (e.g., methane) and oxygen, and other gases present in the oxygen-containing gas fed to the contact zone. Higher hydrocarbons may be recovered from the effluent and, if desired, subjected to further processing using techniques known to those skilled in the art. Unreacted methane may be recovered and recycled to the contact zone.

The invention is further illustrated by reference to the following examples.

EXAMPLES 1-3

A mixed feed containing 50 vol. % of methane and 50 vol. % air was contacted with manganese silicates of the formulae $Mn_7SiO_{12}$, $MnSiO_3$, and $Mn_2SiO_4$ at various temperatures temperatures and a total gas hourly space velocity of 860 hr.$^{-1}$. The manganese silicates were provided as particles of 12-28 mesh. Results presented in the Table include methane conversions and product selectivities calculated on a molar basis. Results are based on gas chromatographic analysis of total reactor effluent collected over a run time of 2 minutes at each temperature shown.

TABLE

| Temp. (°C.) | Example 1 $Mn_7SiO_{12}$ | | Example 2 $MnSiO_3$ | | Example 3 $Mn_2SiO_4$ | |
|---|---|---|---|---|---|---|
| | % $CH_4$ Conv. | % $C_2+$ Sel. | % $CH_4$ Conv. | % $C_2+$ Sel. | % $CH_4$ Conv. | % $C_2+$ Sel. |
| 600 | 4.5 | 2 | 11.7 | 27 | 10 | 31 |
| 650 | 8.5 | 6 | 12.5 | 18 | 13 | 33 |
| 700 | 13. | 32 | 15. | 37 | 15 | 39 |
| 750 | 18. | 49 | 15.2 | 44 | 20 | 59 |
| 800 | 18.5 | 60 | 16.1 | 55 | 25 | 49 |
| 850 | 22.5 | 52 | 16.7 | 60 | 25 | 47 |

What is claimed is:

1. A method for converting methane to higher hydrocarbon products which comprises contacting a hydrocarbon gas comprising methane and an oxygen-containing gas with a contact solid comprising at least one manganese silicate at conditions to convert methane to said products.

2. The method of claim 1 wherein said hydrocarbon gas and said oxygen-containing gas are contacted with said solid at a temperature selected within the range of about 300° to 1200° C.

3. The method of claim 1 wherein said hydrocarbon gas and said oxygen-containing gas are contacted with said solid at a temperature selected within the range of about 500° to 1000° C.

4. The method of claim 1 wherein the manganese silicate is described by the formula $Mn_xSiO_y$ wherein x is an integer selected within the range of 1 to 7 and y has a value which is determined by the valence and proportions of the other elements present in the compound.

5. A method for converting methane to higher hydrocarbon products which comprises contacting hydrocarbon gas comprising methane and an oxygen-containing gas at a temperature within the range of about 300° to 1200° C. with a contact solid which solid comprises a manganese silicate.

6. The method of claim 5 wherein the hydrocarbon gas comprising methane contains from about 40 to about 100 volume percent methane.

7. The method of claim 5 wherein the gas comprising methane contains from about 80 to about 100 volume percent methane.

8. The method of claim 5 wherein the gas comprising methane contains from about 90 to about 100 volume percent methane.

9. The method of claim 5 wherein the gas comprising methane is derived from natural gas.

10. The method of claim 5 wherein the gas comprising methane is derived from processed natural gas.

11. The method of claim 5 wherein the oxygen-containing gas is air.

12. The method of claim 5 wherein said hydrocarbon gas and said oxygen-containing gas are contacted with said solid at a temperature within the range of about 500° to 1000° C.

13. The method of claim 5 wherein the volume ratio of hydrocarbon in said hydrocarbon gas to oxygen in said oxygen-containing gas is within the range of about 0.1-100:1.

14. The method of claim 5 wherein the volume ratio of hydrocarbon in said hydrocarbon gas to oxygen in said oxygen-containing gas is within the range of about 1-50:1.

15. The method of claim 5 wherein said solid comprises at least one member of the group consisting of $Mn_7SiO_{12}$, $MnSiO_3$ and $Mn_2SiO_4$.

* * * * *